United States Patent
Shahkhalili et al.

(10) Patent No.: US 9,402,412 B2
(45) Date of Patent: Aug. 2, 2016

(54) METABOLIC IMPRINTING

(75) Inventors: Yasaman Shahkhalili, La-Tour-de Peilz (CH); Kevin Acheson, Pully (CH); Katherine Mace, Lausanne (CH); Julie Moulin, Attalens (CH); Irene Zbinden, Le Mont sur Lausanne (CH); Olivier Aprikian, Vevey (CH); Theresa Voss, La Tour de Peilz (CH)

(73) Assignee: Nestec S.A., Vevey (CH)

( * ) Notice: Subject to any disclaimer, the term of this patent is extended or adjusted under 35 U.S.C. 154(b) by 1323 days.

(21) Appl. No.: 11/755,589

(22) Filed: May 30, 2007

(65) Prior Publication Data
US 2008/0300195 A1   Dec. 4, 2008

(51) Int. Cl.
*A23C 9/18*   (2006.01)
*A23L 1/29*   (2006.01)
*A61K 31/70*  (2006.01)

(52) U.S. Cl.
CPC ............... *A23L 1/296* (2013.01); *A61K 31/70* (2013.01); *A23V 2002/00* (2013.01)

(58) Field of Classification Search
CPC .................................. A23C 9/18; A23L 1/296
USPC ...................... 514/23; 426/601, 658
See application file for complete search history.

(56) References Cited

U.S. PATENT DOCUMENTS

| | | | |
|---|---|---|---|
| 2,669,641 A * | 2/1954 | Becker | 219/387 |
| 4,859,475 A * | 8/1989 | Michnowski | 426/72 |
| 5,132,113 A * | 7/1992 | Luca | 424/750 |
| 2004/0043106 A1 * | 3/2004 | Anfinsen et al. | 426/2 |
| 2004/0101596 A1 * | 5/2004 | Ndife et al. | 426/72 |
| 2007/0207132 A1 * | 9/2007 | Speelmans et al. | 424/93.45 |
| 2009/0297636 A1 | 12/2009 | Alles | |
| 2010/0255114 A1 | 10/2010 | Shahkhalili et al. | 424/535 |

OTHER PUBLICATIONS

Food and Nutrition Board, "Dietary Intakes for Energy, Carbohydrate, Fibre, Fat, Fatty Acids, Cholesterol, Protein, and Amino Acids," Institute of Medicine of the National Academies, The National Academic Press, Washington, D.C., 2005.
Kislyakovskaya, V.G. et al., "Nutrition of Infants and Preschool Children," Moscow Prosveschenie Publishing House 1983, pp. 133-167,52-53.
Uauy, R. et al.: "Lipid requirements of infants: implications for nutrient composition of fortified complementary foods." Journal of Nutrition, vol. 133, 2003, pp. 2962S-2972S, XP002471984.
Di Toro, R.: "Follow-on formulae", Acta Paediatrica Suppl, vol. 402, 1994, pp. 46-49, XP002471988, tables 1, 2, p. 47, col. 1, paragraph 1.
Milner, J. et al.: "The role of dietary fat in child nutrition and development." Journal of Nutrition, vol. 129, 1999, pp. 2094-2105, XP002471986, p. 2101, col. 2, last paragraph—p. 2102, col. 2, paragraph 4.
Aggett, P. et al.: "Comment on the composition of cow's milk based on follow-up formulas", Acta Paediatrica Scand, vol. 79, 1990, pp. 250-254, XP002471987, p. 2, paragraph 3—p. 4, paragraph 3.
Butte, N. et al.: "The start healthy feeding guidelines for infants and toddlers." Journal of the American Dietetic Association, vol. 104, No. 3, 2004, pp. 442-454, XP002471985, tables 1-2, p. 47, col. 1, paragraph 1.
Mace K, Shahkhalili Y, Aprikian O, Stan S: "Dietary fat and fat types as early determinants of childhood obesity: a reappraisal", Nature, vol. 30, 2006, pp. S50-S57, XP002496959; abstract; p. S51, col. 2, paragraph 1-3; tables 1,2; p. S53, col. 1, paragraph 2.

* cited by examiner

*Primary Examiner* — Fereydoun G Sajjadi
*Assistant Examiner* — Everett White
(74) *Attorney, Agent, or Firm* — Gary M. Lobel, Esq.

(57) ABSTRACT

The present invention generally relates to the field of nutrition. In particular the present invention relates to infant nutrition in the post natal period and in early life, more particular during the age period of 6-36 months or during a part thereof. One embodiment of the present invention is a kit of diet compositions for children during the age period of 6-36 months or during a part thereof, wherein the macronutrient content of the compositions is gradually changing in the form of a straight line from a composition that comprises about 40-50% energy from fat and about 40-49% energy from carbohydrates for children at the age of 6 months to a composition that comprises about 30-35% energy from fat and about 50-55% energy from carbohydrates for children at the age of 36 months, and its use to prevent obesity later in life.

22 Claims, 5 Drawing Sheets

METABOLIC IMPRINTING

BACKGROUND

The present invention generally relates to the field of nutrition. In particular the present invention relates to infant nutrition in the post natal period and in early life, more particular during the age period of 6-36 months or during a part thereof.

SUMMARY

Evidence is accumulating that nutrition during early life can program the development of diseases later in life[1], a discovery that was named "metabolic programming or imprinting". This evidence, mainly driven from foetal development in-utero[2-7], reveals the importance of optimal nutrition during early life for the health of the individual later in the life. Considering that many developmental processes still continue during early post natal life, it is evident that postnatal nutrition—especially during suckling and during the complementary feeding period—plays an important role for the health status and for the prevention of diseases later in life.

Prior evidence in rats demonstrates that a change in the fat and carbohydrate (CHO) content of milk during the suckling period may have an impact on the development of obesity and diabetes later in life. In these studies[8-9] that relate to breast feeding without additives rats were artificially reared by using either a milk substitute formula low in fat content (LF) and rich in CHO (20% total energy from fat (fat E) and 56% total energy from carbohydrates (CHO E), respectively) or by using a milk composition similar to rat milk, namely high in fat (HF) and low in CHO (8% CHO E and 68% fat E) or were mother-fed from the age of 4 to 24 days postnatal. All groups were weaned onto a low fat laboratory standard chow diet. The LF feeding during the suckling period resulted in hyperinsulinemia which persisted into adulthood and lead to an increase in body weight and onset of adult obesity, an effect termed "metabolic programming"[10-11]. Beyond total milk feeding (suckling period) this effect was previously not investigated to the inventor's best knowledge.

Although during the suckling period "milk" as the first diet of infants and other mammals is very rich in fat (50% of energy from fat), the dietary fat intake is reduced considerably during the complementary feeding period as an infant is gradually weaned off milk onto semi solid foods.

This is due to the replacement of high-fat milk with weaning foods low in fat content, such as fruits, vegetables, weaning cereals, fruit juices etc.

It has been reported that the fat intake of infants, even in developed countries, is low (30% of energy from fat) during the complementary feeding period (6-12 months)[12-13]. Indeed the complementary feeding period has been referred to as "the period of life with the lowest fat intake during the life cycle of man".

Data concerning nutritional recommendations for humans during the weaning period are scarce and recommendations are mainly based on estimates of the nutritional requirements of those of suckling infants adjusted for weight and energy intake. Infant nutrition during this period of rapid growth is surrounded by uncertainties and there is little agreement about what should constitute an optimal composition of the complementary diet and in particular an optimal fat and carbohydrate content of complementary diets.

The present uncertainty about the long-term consequences of the fat and CHO content of the weaning diet on health in general and—in particular—on development of obesity later in life led the present inventors to investigate these consequences in rats as model system for humans.

It is an advantage of the present invention to provide a nutritional concept for the transition period from nutrition with breast milk or breast milk-like products in terms of fat and CHO content during the suckling period to the subsequent nutrition with baby food that allows it to reduce the risk that the child develops a bad health status, in particular obesity and diabetes later in life.

The present invention provides kits, methods of reducing the risk of obesity and mealplans.

In one embodiment the present invention relates to a kit of parts comprising diet compositions for children during the age period of 6-36 months or during a part thereof. In an embodiment, the macronutrient content of the compositions is gradually changing in the form of a straight line from a composition that comprises about 40-50% energy from fat and about 40-49% energy from carbohydrates for children at the age of 6 months to a composition that comprises about 30-35% energy from fat and about 50-55% energy from carbohydrates for children at the age of 36 months.

A wide variety of kits and methods of using the kit are possible and envisioned by the present invention.

Additional features and advantages are described herein, and will be apparent from, the following Detailed Description and the figures.

DETAILED DESCRIPTION

% energy refers for the purpose of the present invention always to the K total amount of energy that is present in a diet composition. A diet composition that has 33% energy from fat will therefore have 67% energy from carbohydrates and/or proteins.

A diet composition means at least one meal or a part thereof. For example, a diet composition can be a complete meal such as breakfast, lunch or dinner. It can also be one or more, e.g. five, individual meals that are consumed during the day. It can also be more than one individual meal. It can also represent only a part of an individual meal or a part of more individual meals. It is preferred that the diet compositions of the present invention represent individual meals. Oftentimes dinner represents a substantial part of the diet on a caloric basis. In infants, the caloric intake during dinner can range from 15 to 35% of the daily caloric intake. Hence, in a preferred embodiment the meals are dinners. Dinners are the main meal of the day and can be served in the evening or at midday. Nutritionally well-balanced dinners can, hence, significantly contribute to the health of infants.

Macronutrients are those nutrients that together provide most metabolic energy to an organism. For the purpose of the present invention the three macronutrients are carbohydrates, proteins, and fats.

Figure 1:
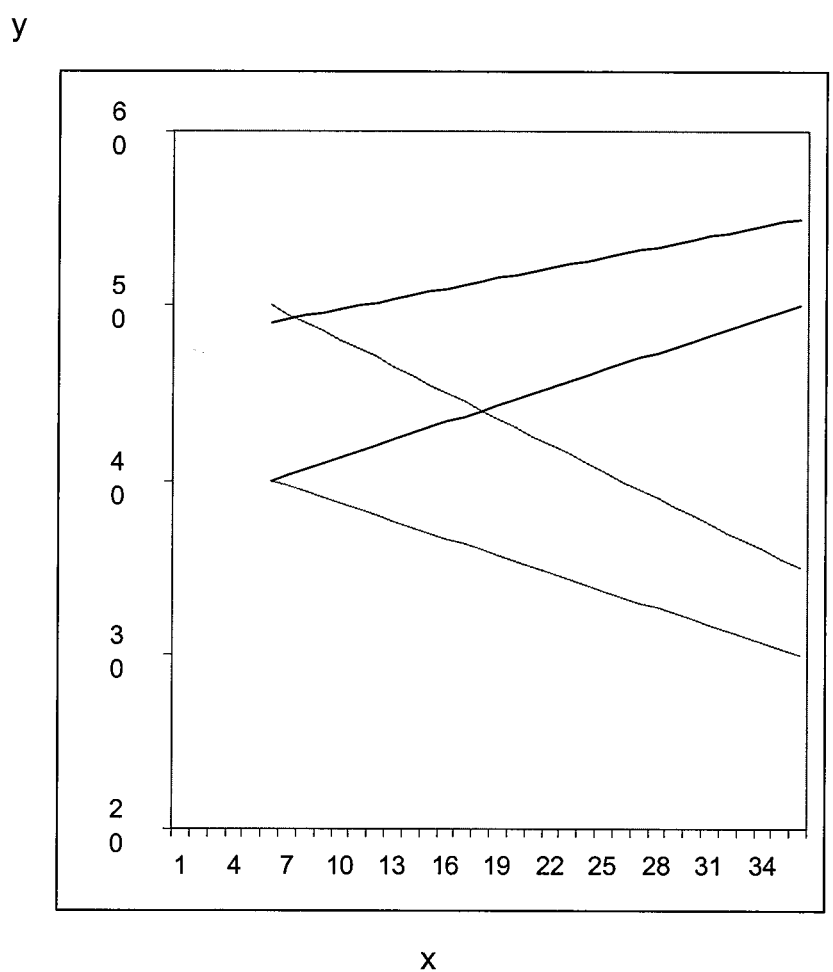
FIG. 1 shows the % energy content of fat (grey lines) and carbohydrates (black lines) of the total energy content of the diet composition depending on the age of the child in month. The x-axis shows the age of the child in month and the y-axis shows the %-energy content of the diet composition.

Gradually changing in the form of a straight line from a composition that comprises about 40-50% energy from fat and about 40-49% energy from carbohydrates for children at the age of 6 months to a composition that comprises about 30-35% energy from fat and about 50-55% energy from carbohydrates for children at the age of 36 months means any straight line or group of straight lines that is located on and/or between the two black lines in FIG. 1 for carbohydrates and any straight line that is located on and/or between the two grey lines in FIG. 1 for fats. The present invention comprises all possible kits of diet compositions that are represented by FIG. 1 and all such kits of diet compositions are disclosed by FIG. 1.

Expressed in mathematical terms this means that the present invention discloses and comprises every kit of diet compositions for children during the age period of 6-36 months or during a part thereof, wherein the fat content of the diet composition is adjusted to any straight line, which is located on or between the straight lines $y=-1/2x+53$ and $y=-1/3x+42$ (y is % energy from fat), and wherein the carbohydrate content of the diet composition is adjusted to any straight line, which is located on or between the straight lines $y=1/5x+47.8$ and $y-1/3x+38$ (y is % energy from carbohydrates)

between x=6 and x=36, if x is the age of the child in months.

A kit of parts in accordance with the present invention provides a tool for the parents to improve infant nutrition in an optimal way without having to keep detailed records of the nutritional components that the infant has already ingested.

The present method and kit thus increase convenience and reduce the occurrence of consequences of non-optimal nutrition.

"Infants" as used in the present invention are in particular human children aged from 4 months to 3 years. The present method is particularly directed at infants aged from 6 to 36 months.

In one embodiment of the present invention the diet compositions are daily diet compositions. Daily diet compositions have the advantage that they can be used very effectively to tightly regulate the gradual change of the fat and carbohydrate content of the food of a child when it is gaining age. It is important to note that if the diet compositions are daily diet compositions the individual meals may well deviate somewhat from a macronutrient content that is gradually changing in the form of a straight line from a composition that comprises about 40-50% energy from fat and about 40-49% energy from carbohydrates for children at the age of 6 months to a composition that comprises about 30-35% energy from fat and about 50-55% energy from carbohydrates for children at the age of 36 months, as long as the individual meals to be consumed during a day together—that together are considered a daily diet composition—fulfil this requirement.

This way it is possible to adapt a mealplan of a child, e.g., in a way that it can consume food that is easy to digest in the evening to allow an easy sleep, while it consumes food compositions that are more difficult to digest during the day.

In one embodiment of the present invention the total energy content of the composition is gradually changing in the form of a straight line from a composition that comprises about 670-715 kcal/day for children at the age of 6 months to a composition that comprises about 1000-1200 kcal/day for children at the age of 36 months. This allows adapting the energy content of the diet compositions to the particular age of the child, so that it can be assured that a sufficient amount of energy is always present during this decisive period of development of the child, while an overfeeding is avoided.

Changing gradually means in one embodiment of the present invention that the fat and carbohydrate content of the diet composition is adjusted daily, based on the age of the child and the corresponding optimal fat content and carbohydrate content of the composition. Optionally, the total energy content is also adjusted daily along with the fat and carbohydrate content. This results in a very gradual change without any noticeable "steps" in diet composition. Consequently, the infant's organism will not have to adapt to any abrupt changes in food content.

In another embodiment of the present invention changing gradually means that the content of the diet composition is adjusted weekly, based on the age of the child and the corresponding optimal fat content and carbohydrate content of the composition. Also in this case the changes that are made to the diet composition are so marginal that the metabolism of the infant will not be faced with any abrupt changes.

In another embodiment of the present invention changing gradually means that the content of the diet composition is adjusted monthly, based on the age of the child and the corresponding optimal fat content and carbohydrate content of the composition. Even if the adjustment of the diet composition is made on a monthly level the resulting mealplan of a child will exhibit a smooth transition from a high fat-low carbohydrate composition at the age of 6 months to a low fat-high carbohydrate composition at the age of 36 months without any abrupt changes.

The present inventors have found that the object of the present invention can still well be achieved by adjusting the macronutrient content of the diet composition stepwise, based on the age of the child and the corresponding optimal fat content and carbohydrate content of the composition as detailed above, preferably in 3-10 steps, most preferred in 3-4 steps during the age of 6-36 months.

This stepwise adjustment is preferable made at a child age of 6, 8, 12, 18, 24 and/or 36 months.

In one preferred embodiment of the present invention changing gradually includes that the content of the diet composition is adjusted also with respect to the total calorie content based on the age of the child and the corresponding optimal calorie content of the composition.

For example, a kit according to the present invention can comprise at least one diet composition that comprises about 44-46% energy from fat and about 47-49% energy from carbohydrates during the age of 6-8 months, at least one diet composition that comprises about 39-41% energy from fat and about 49-52% energy from carbohydrate during the age of 8-12 months, and/or at least one diet composition that comprises about 34-35% energy from fat and about 51-53% energy from carbohydrate during the age of 12-36 months. Preferably, the at least one diet composition for consumption during the age of 6-8 months comprises about 670-715 kcal/day, the at least one diet composition for consumption during the age of 8-12 months comprises about 715-850 kcal/day, and/or the at least one diet composition for consumption during the age of 12-36 months comprises about 750-1200 kcal/day.

The diet compositions of the present invention further comprise a protein source. The amount of protein source present is preferably adjusted to the need of the child of the particular age in question and can generally be calculated as follows:

% energy from protein=100−(% energy from fat+% energy from carbohydrates)

In a particular preferred embodiment of the present invention the content of carbohydrates in the compositions is gradually changing from a composition that comprises about 48% energy from carbohydrates for children at the age of 6 months to a composition that comprises about 53% energy from carbohydrates for children at the age of 36 months.

Generally the kit of the present invention comprises at least one, preferably at least two diet compositions. A diet composition preferably constitutes one or more complete meals, one or more parts of a complete meal or one or more snacks or a part thereof.

The number of diet compositions the kit of the present invention can contain is not particularly limited and is only regulated by the storage stability of the food product. Hence, a kit intended for use in a nursery or in a hospital can be significantly larger than a kit for private households.

In a preferred embodiment the kit of the present invention comprises diet compositions for at least one day. In this respect the kit might comprise 2 or more, preferably 3-10, even more preferred 5 individual meals. The daily food intake can, e.g., be divided into three meals and 2 up to 3 snacks. More meals with corresponding smaller portions have the advantage that the child's metabolism will not be faced with too large amount of food and at the same time periods with an "empty stomach" are avoided.

In further embodiments of the present invention the kit comprises diet compositions for three days, for a week or for a month. It is preferred that the diet compositions represent one or more individual meals. In this case the kit can for example comprise at least 3, preferably 3-21, most preferred 9 individual meals.

It is further preferred that the diet compositions represent a total diet, which is to be understood as sum of food to be consumed by a person over a given period of time.

Preferably, the diet composition of the present invention also comprises micronutrients and/or minerals to arrive at an ideally balanced food product for the child at the particular age. Also these components can preferably be varied based on the specific needs of the child at a particular age.

In a preferred embodiment of the present invention the fat component comprises essential fatty acids. Essential fatty acids are fatty acids that cannot be produced by the body. They are capable of fulfilling important functions in the human body. Two families of essential fatty acids are in particular important, the omega-3 and the omega-6 family. Alpha-linolenic acid (ALA, a fatty acid with a chain length of 18 carbon atoms and containing three double bonds) is an example of a member of the omega-3 family. ALA is, e.g., found in flaxseed and various vegetable oils and nuts. An example of a member of the omega-6 family of essential fatty acids is linoleic acid (LA, a fatty acid with a chain length of 18 carbon atoms and containing two double bonds). The weight ratio of omega-6/omega-3 fatty acids in the diet compositions of the present invention is preferably between 5 and 15.

Preferably, the diet compositions of the present invention are of a liquid nature. Preferred embodiments have a consistency of a liquid or of a mash. This can be achieved by the presence of water in the diet compositions of the present invention. Preferably, they contain between 75 and 90 wt-% water based on the total weight of the diet composition, more preferably between 78 and 85 wt-% water.

In a preferred embodiment, the diet compositions to be administered to the infants each have a volume between 90 and 500 ml, more preferably between 125 and 300 ml. The diet compositions of the present invention may all have about the same volume (i.e. difference between greatest and smallest volume is less than 50 ml) or they may have increasing volumes with the increasing age of the child to reflect an increased caloric content.

Preferably, the diet compositions of the present invention are to be consumed at a temperature of between 15 and 55° C., more preferred between 30 and 50° C., and even more preferably between 35 and 45° C.

The diet compositions according to the present invention are preferably individually packaged and provided as a kit of parts. The kit of parts contains in one embodiment several different meals. The diet compositions in the kit are preferably in ready-to-eat and/or dried form. From the dried form, a ready-to-eat form can be easily produced by reconstitution in a suitable liquid, e.g. water. The ready-to-eat form can normally be administered directly to the infant, optionally after heating and/or mixing.

The present invention relates also to the use of a series of diet compositions, wherein the macronutrient content of the compositions is gradually changing from a composition that comprises about 40-50% energy from fat and about 40-49% energy from carbohydrates for children at the age of 6 months to a composition that comprises about 30-35% energy from fat and about 50-55% energy from carbohydrates for children at the age of 36 months for the preparation of a kit to prevent the development of obesity.

The kit that is to be prepared by the use of the present invention can be any kit of the present invention and can have any feature or any combination of features as described herein.

The series of diet compositions comprises 2 or more individual diet compositions, preferably 3-35 diet compositions.

Finally, the present invention also relates to a mealplan for children that comprises a kit of the present invention. The mealplan is intended for the prevention of obesity later in life.

Those skilled in the art will understand that it is possible to freely combine features and embodiments of the present invention as described herein without departing from the scope of the present invention as disclosed.

By way of example and not limitation, examples of the present invention will now be given.

EXAMPLES

Experiment 1

The consequence of fat and CHO content of weaning diet on the later development of obesity was investigated using rats.

Seventy two male Sprague-Dawley rats were separated from their dam at the age of 16 days. The animals were divided into three study groups (24 animals/group) and were pair-fed, on an iso-energetic and iso-protein basis, with one of the following weaning diets (Table 1) differing only in energy distribution from Fat and CHO as: (% energy) 10/70 (group A); 30/50 (group B) and 60/20 (group C). for 20 days (Phase I: age 16 to 36 days). All groups were then fed ad libitum with a standard low-fat commercial chow diet (Kliba 3434, 13% fat E:) for 20 weeks (phase II: age 5 to 25 weeks), after which all groups were challenged with a high-fat diet (45% fat E: Kliba 2126) that was fed ad-libitum for a period of 18 weeks (phase III: age 35 to 53 weeks).

TABLE 1

Composition of weaning diets

| PRODUITS | A g/345 Kcal | B g/345 Kcal | C g/345 Kcal |
|---|---|---|---|
| Casein | 20 | 20 | 20 |
| L-Cystine | 0.3 | 0.3 | 0.3 |
| Lactose.H2O | 5 | 5 | 5 |
| Sucrose | 10 | 10 | 10 |
| Corn starch | 51.1490 | 31.618 | 2.42700 |
| Vit. Mix AIN93 | 1 | 1 | 1 |

TABLE 1-continued

Composition of weaning diets

| PRODUITS | A<br>g/345 Kcal | B<br>g/345 Kcal | C<br>g/345 Kcal |
|---|---|---|---|
| Min. Mix AIN93 G* | 3.5 | 3.5 | 3.5 |
| Bitartr. choline | 0.25 | 0.25 | 0.25 |
| Tert-butylhydroquinone | 0.0014 | 0.0014 | 0.0014 |
| Cellulose | 5 | 5 | 5 |
| Soya oil | 1.90 | 5.741 | 11.482 |
| Corn oil | 1.90 | 5.741 | 11.482 |
| Total | 100 | 88.15 | 70.44 |
| % Energy | | | |
| Protein | 20 | 20 | 20 |
| CHO | 70 | 50 | 20 |
| Fat | 10 | 30 | 60 |

Food intake was measured daily during the weaning period (period I) and twice per week during the post-weaning periods (period II &III). Body weight was measured 2-3 times per week throughout the study.

The body composition, which is body fat and fat free mass, was measured during post weaning phases II and III using NMR imaging (EchoMRI 2004), at 27, 35, 47 and 52 weeks of age.

Figure 2:
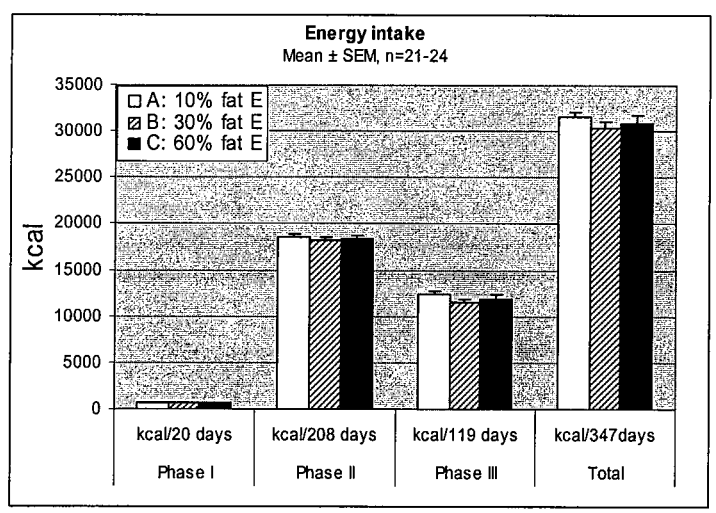
FIG. 2 shows the energy intake during all study phases, phase I, phase II, phase III and the overall energy intake of Experiment I.
Figure 3:
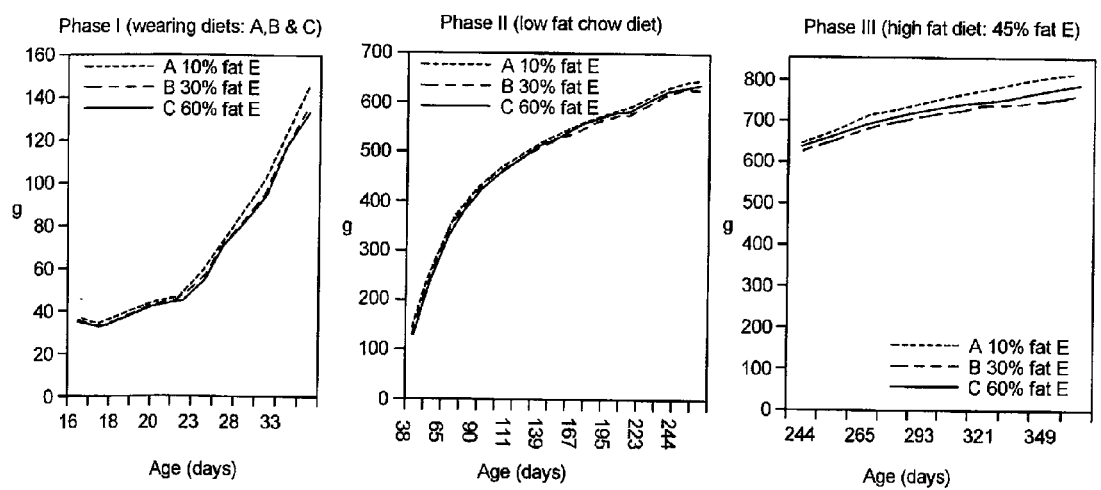
FIG. 3 shows the development of the body weights of the test animals during each study phase, phase I, phase II and phase III during Experiment I.

FIGS. 2-3 demonstrate that the energy intakes and body weights of all groups fed the weaning diets with different Fat/CHO ratios were similar at the end of the weaning period (phase I), during 9 months of low-fat diet (phase II) as well as during the 4 months of the obesigenic, high-fat challenge (45% fat E) feeding period, (Phase III).

Figure 4:
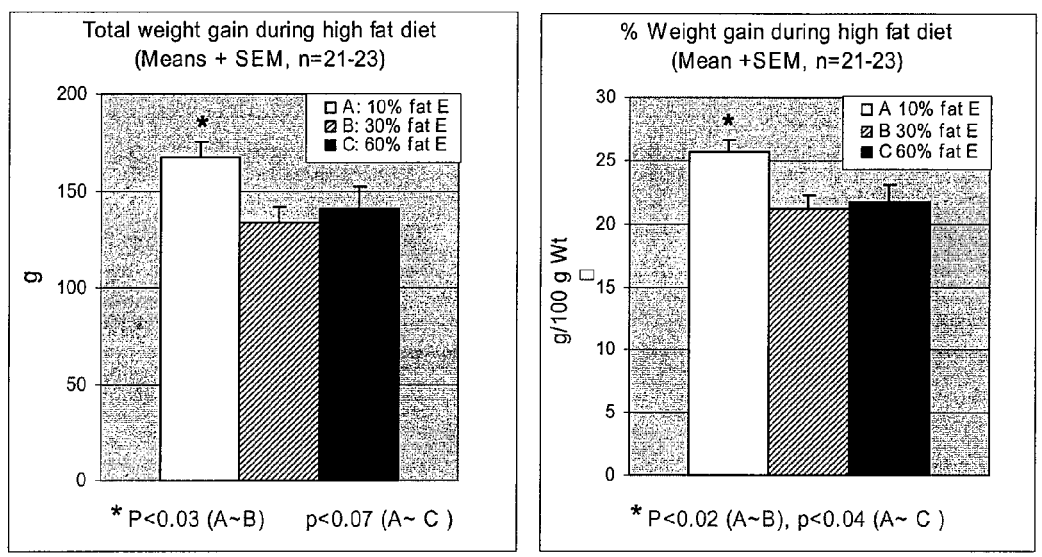
FIG. 4 shows the weight gain of the different groups of test animals during high fat period (Phase III) in Experiment I.
Figure 5:
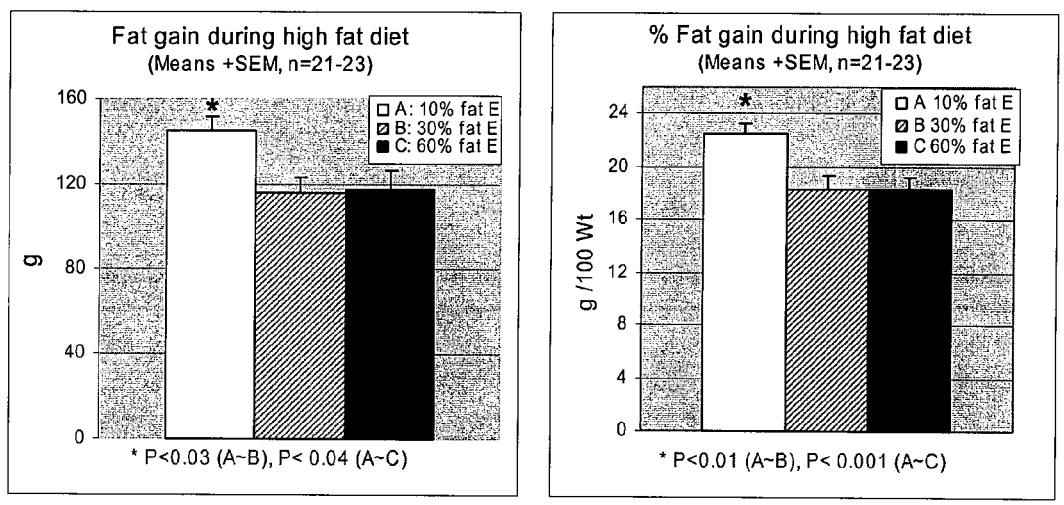
FIG. 5 shows the fat gain of the different groups of test animals during high fat period (Phase III) in Experiment I.

However, the rats fed with a low-fat (10% E), high-carbohydrate (70% E), diet only during 19 days weaning period gained significantly more body weight (FIG. 4) and body fat (FIG. 5) during the high-fat challenge diet at adult age (age of 35 to 53 weeks), relative to the other 2 groups fed with higher fat (30% & 60% E) and lower CHO (50% or 20% E) diets only during weaning period (p<0.05).

These results show that a weaning diet with a macronutrient composition (fat and CHO) close to that consumed during the suckling period (high fat diet) has a beneficial effect toward reducing the risk of development of obesity later in life, while a high-CHO, low-fat diet during the weaning period increases the susceptibility to excess body weight and fat mass gain later in life.

The inventors believe that this is the first report on "metabolic programming" during the complementary feeding period and reveals the importance of the Fat/CHO content of complementary diet for obesity prevention later in life.

In the following sample diet compositions are provided for the age period of 6-8 months (*=carbohydrates as monosaccharides):

Menu 1:

| | g<br>ml (milk) | Energy<br>kcal | Protein g | Fat g | CHO* g |
|---|---|---|---|---|---|
| Total Breast milk/day | 780 | 540.8 | 6.73 | 32.97 | 57.9 |
| Breakfast | | | | | |
| Rice cereal fortified with Fe (prepared with 160 ml Breast milk/ infant formula) Snack | 20 | 76.4 | 1.6 | 0.18 | 17 |
| carrots puree | 30 | 6.6 | 0.17 | 0.12 | 1.3 |
| Lunch | | | | | |
| Baby meat (Turkey) Snack | 30 | 22.8 | 2.86 | 1.16 | 0.02 |
| Green beans puree Snack | 25 | 6.25 | 0.43 | 0.03 | 1.18 |
| Banana puree | 60 | 57 | 0.72 | 0.18 | 13.9 |
| Total per day | | kcal/day<br>710 | g/day<br>13 | g/day<br>35 | g/day<br>91 |
| % Energy | | | 7 | 44 | 48 |

Menu 2:

| | g<br>ml (milk) | Energy<br>kcal | Protein g | Fat g | CHO* g |
|---|---|---|---|---|---|
| Breast milk Breakfast | 780 | 540.8 | 6.73 | 32.97 | 57.9 |
| Rice cereal fortified with Fe (prepared with 160 ml Breast milk/ infant formula) Lunch | 20 | 76.4 | 1.6 | 0.18 | 17 |
| Baby meat (Veal) Snack | 30 | 30.3 | 4.05 | 1.44 | 0 |
| Pumpkin puree Snack | 60 | 7.8 | 0.42 | 0.12 | 1.32 |
| Pears puree | 60 | 24.6 | 0.12 | 0.06 | 6.24 |
| Total per day | | kcal/day<br>680 | g/day<br>13 | g/day<br>35 | g/day<br>82 |
| % Energy | | | 8 | 46 | 45 |

Menu 3:

| | g<br>ml (milk) | Energy<br>kcal | Protein g | Fat g | CHO* g |
|---|---|---|---|---|---|
| Breast milk Breakfast | 780 | 540.8 | 6.73 | 32.97 | 57.9 |
| Wheat baby cereal fortified Fe (prepared with 120 ml Breast milk/ infant formula) Lunch | 15 | 56.85 | 1.8 | 0.195 | 12 |
| Carrots and Chicken baby meal Snack | 100 | 65 | 2.7 | 1.4 | 10.2 |
| Mixed fruit puree | 50 | 27.5 | 0.35 | 0.05 | 6.9 |
| Total per day | | kcal/day<br>690 | g/day<br>11.6 | g/day<br>34.6 | g/day<br>87.0 |
| % Energy | | | 7 | 45 | 47 |

| Menus (6-8 months with breast milk) | | | | |
|---|---|---|---|---|
| | Menu 1 | Menu 2 | Menu 3 | Range |
| Energy (kcal) | 710 | 680 | 690 | 680-710 |
| Protein (g) | 13 | 13 | 12 | 12-13 |
| Fat (g) | 35 | 35 | 35 | 35.0 |
| CHO (g) | 91 | 82.5 | 87.0 | 82-93 |
| % Energy (E) | % E | % E | % E | % E |
| Protein | 7 | 8 | 7 | 7-8 |
| Fat | 44 | 46 | 45 | 44-46 |
| CHO | 48 | 45 | 47 | 45-48 |

In the following sample diet compositions are provided for the age period of 8-12 months (*=carbohydrates as monosaccharides):

Menu 1:

| | g ml (milk) | Energy kcal | Protein g | Fat g | CHO* g |
|---|---|---|---|---|---|
| Total Breast milk/day Breakfast | 600 | 416.0 | 5.2 | 25.4 | 44.5 |
| Wheat baby cereal fortified with Fe (Prepared with 160 ml Breast milk/ infant formula) | 20 | 75.8 | 2.4 | 0.26 | 16 |
| Mashed Banana Lunch | 20 | 19 | 0.24 | 0.06 | 4.63 |
| Baby meat (Turkey) | 20 | 22.8 | 2.86 | 1.16 | 0.02 |
| Pumpkins | 80 | 10.4 | 0.56 | 0.16 | 1.76 |
| Potato puree with butter Snack | 70 | 72.8 | 1.26 | 3.01 | 9.3 |
| 2 baby Biscuits | 21.5 | 85 | 1.5 | 1.9 | 15.5 |
| Sliced apricot | 30 | 9.3 | 0.27 | 0.03 | 2.16 |
| Raspberry | 30 | 7.5 | 0.42 | 0.09 | 1.4 |
| Apple | 30 | 14 | 0.12 | 0.03 | 3.5 |
| Total per day | ml/day | kcal/day 733 | g/day 15 | g/day 32 | g/day 99 |
| % Energy | | | 8 | 39 | 51 |

Menu 2:

| | g ml (milk) | Energy kcal | Protein g | Fat g | CHO* g |
|---|---|---|---|---|---|
| Total Breast milk/day Breakfast/dinner | 600 | 416.0 | 5.2 | 25.4 | 44.5 |
| Baby 8 cereals fortified with Fe (Prepared with 160 ml Breast milk/ infant formula) | 20 | 77.4 | 1.84 | 0.26 | 16.9 |
| Sliced mango Lunch | 30 | 17.1 | 0.21 | 0.06 | 4.23 |
| Papa baby meat with vegetables and pasta | 250 | 150 | 6.5 | 3.75 | 22.75 |

Menu 2:

| | g ml (milk) | Energy kcal | Protein g | Fat g | CHO* g |
|---|---|---|---|---|---|
| Snack | | | | | |
| Milky baby dessert with fruit | 130 | 88.4 | 1.3 | 1.04 | 18.38 |
| Diced cooked peaches + 5 g whipping cream | 60 | 64.8 | 0.6 | 5.6 | 4.56 |
| Total per day Menu 2 with Breast milk | ml/day | kcal/day 814 | g/day 16 | g/day 36 | g/day 111 |
| % Energy | | | 8 | 40 | 51 |

Menu 3:

| | g ml (milk) | Energy kcal | Protein g | Fat g | CHO* g |
|---|---|---|---|---|---|
| Total Breast milk/day Breakfast | 600 | 416.0 | 5.2 | 25.4 | 44.5 |
| Rice cereal fortified with Fe (Prepared with 160 ml Breast milk/ infant formula) Lunch | 20 | 76.4 | 1.6 | 0.18 | 17 |
| Ground (mine) beef | 25 | 55.3 | 4.7 | 4.1 | 0.0 |
| Carrots puree | 50 | 11 | 0.3 | 0.2 | 2.2 |
| Rice (+2 g olive oil) Dinner | 50 | 87 | 1.3 | 2.63 | 15.43 |
| Milk based soup with legumes | 200 | 104 | 4.8 | 2.72 | 15.36 |
| Whole grain toasted bread Snack | 12.5 | 26.9 | 1.2 | 0.3 | 5.2 |
| Apple puree | 30 | 14 | 0.12 | 0.03 | 3.5 |
| Diced melon (cantaloupe) | 60 | 11.4 | 0.36 | 0.06 | 2.52 |
| Total per day Menu 3 with Breast milk | ml/day | kcal/day 802 | g/day 19 | g/day 36 | g/day 106 |
| % Energy | | | 10 | 40 | 49 |

| Menus 8-12 months with breast milk | | | | |
|---|---|---|---|---|
| | Menu 1 | Menu 2 | Menu 3 | Range |
| Energy (kcal) | 732.6 | 813.7 | 801.9 | 733-814 |
| Protein (g) | 14.8 | 15.6 | 19.5 | 15-21 |
| Fat (g) | 32.1 | 36.1 | 35.5 | 32-37 |
| CHO (g) | 98.8 | 111.4 | 105.7 | 99.111 |
| % Energy (E) | % Energy | % Energy | % Energy | % Energy |
| Protein | 8 | 8 | 10 | 8-10 |
| Fat | 39 | 40 | 40 | 39-41 |
| CHO | 51 | 51 | 49 | 49-51 |

In the following sample diet compositions are provided for the age period of 12-36 months (*=carbohydrates as monosaccharides):

Menu 1:

| | g ml (milk) | Energy kcal | Protein g | Fat g | CHO* g |
|---|---|---|---|---|---|
| Breakfast | | | | | |
| Junior Fe fortified Oat cereal with, banana, pear | 25 | 100.0 | 3.75 | 2.75 | 15 |
| Prepared with 160 ml Growing up milk | 160 | 110.0 | 2.73 | 4.96 | 13.6 |
| Fresh blackberries | 30 | 7.6 | 0.27 | 0.06 | 1.5 |
| Lunch | | | | | |
| tomato sauce with 4 g olive oil | 35 | 41.2 | 0.2 | 4.09 | 0.9 |
| cooked noodles | 100 | 65.3 | 2.2 | 0.5 | 13 |
| Growing up milk | 150 | 103.1 | 2.56 | 4.65 | 12.75 |
| Snack | | | | | |
| Diced Kiwi | 60 | 30.8 | 0.7 | 0.3 | 6.4 |
| Dessert Caramel (Petit Gourmand) | 100 | 94.6 | 3.1 | 3 | 13.8 |
| Dinner | | | | | |
| courgette fried in corn oil | 50 | 26.8 | 1.3 | 2.4 | |
| Diced potatoes | 100 | 76.1 | 1.8 | 0.1 | 17.0 |
| Pork | 15 | 49.5 | 4.3 | 3.6 | |
| Snack | | | | | |
| Wafer biscuits | 20 | 107 | 0.94 | 6 | 13.2 |
| Apples | 60 | 33.5 | 0.24 | 0.06 | 8 |
| Growing up milk | 120 | 82.3 | 2 | 3.72 | 10.2 |
| Total per day | | kcal/day 928 | g/day 26 | g/day 36 | g/day 125 |
| (% Energy) | | | 11 | 35 | 54 |

Menu 2:

| | g ml (milk) | Energy kcal | Protein g | Fat g | CHO* g |
|---|---|---|---|---|---|
| Breakfast | | | | | |
| Growing up milk | 125 | 88 | 2.14 | 3.88 | 10.63 |
| 1 small egg boiled | 30 | 44 | 3.75 | 3.24 | 0 |
| Sliced whole wheat bread | 25 | 54 | 2.3 | 0.625 | 10.4 |
| Butter (unsalted) | 5 | 37 | 0.02 | 4.08 | 0 |
| Sliced Mango | 30 | 17 | 0.0 | 0.0 | 0.4 |
| Snack | | | | | |
| Raspberries | 60 | 15 | 0.84 | 0.18 | 2.76 |
| Lunch | | | | | |
| Growing up milk | 120 | 84 | 2 | 3.7 | 10.2 |
| Sliced whole wheat bread | 25 | 54 | 2.3 | 0.6 | 10.4 |
| Mayonnaise (made with whole milk) | 8 | 55 | 0.1 | 6.0 | 0.1 |
| Tuna in oil | 15 | 28 | 4 | 1.4 | |
| Sliced banana | 50 | 48 | 0.6 | 0.2 | 11.6 |
| Snack | | | | | |
| Milky baby dessert with fruit | 130 | 88.4 | 1.3 | 1.04 | 18.38 |
| Dinner | | | | | |
| Diced beef meat | 15 | 33 | 4.6 | 1.65 | 0 |
| mashed potatoes | 100 | 104 | 1.8 | 4.3 | 15.5 |
| Spinach | 50 | 9 | 1.1 | 0.4 | 0.4 |
| Snack | | | | | |
| Cereal milk drink with fruit | 250 | 240 | 6.5 | 6.5 | 37.5 |
| Total per day | | kcal/day 998.2 | g/day 33.4 | g/day 37.8 | g/day 128.2 |
| % Energy | | | 13 | 34 | 51 |

Menu 3:

| | g ml (milk) | Energy kcal | Protein g | Fat g | CHO* g |
|---|---|---|---|---|---|
| Breakfast | | | | | |
| Growing up milk | 120 | 84 | 2 | 3.72 | 10.2 |
| Ready to eat cereal | 50 | 38.5 | 1.035 | 1.62 | 4.95 |
| Diced orange | 60 | 22.2 | 0.66 | 0.06 | 5.1 |
| Snack | | | | | |
| 4 toddler biscuits* | 43 | 170 | 3 | 3.8 | 31 |
| Apple grape juice (ml) | 120 | 45.6 | 0.12 | 0.12 | 11.9 |
| Lunch | | | | | |
| Growing up milk (1.71 g true protein/100 ml) | 120 | 84 | 2 | 3.72 | 10.2 |
| Ground beef | 20.0 | 44 | 3.7 | 3.2 | 0.0 |
| Diced green beans | 50 | 12 | 0.85 | 0.05 | 2.35 |
| Rice with 7 g olive oil | 105 | 201 | 2.6 | 8.3 | 30.9 |
| Snack | | | | | |
| Cubed cheese | 15 | 49.5 | 3.12 | 4.05 | 0.135 |
| 4 Whole grain crackers | 20 | 82.6 | 2.02 | 2.26 | 14.4 |
| Dinner | | | | | |
| Growing up milk (1.71 g true protein/100 ml) | 120 | 84 | 2 | 3.7 | 10.2 |
| Turkey (50 g) | 20 | 21.2 | 4.4 | 0.4 | 0 |
| Vegetable mix (potato, corn, carrot) | 190 | 105 | 2.7 | 2.5 | 18 |
| Olive oil | 5 | 45 | | 5.0 | |
| Snack | | | | | |
| Fruit cocktail | 130 | 71.51 | 0.91 | 0.13 | 17.94 |
| Total per day | | kcal/day 1161 | g/day 31.1 | g/day 42.7 | g/day 167.2 |
| % Energy | | | 11 | 33 | 54 |

Menus 12-36 months with growing up milk

| | Menu 1 | Menu 2 | Menu 3 | Range |
|---|---|---|---|---|
| Energy (kcal) | 928 | 998.2 | 1161 | 928-1160 |
| Protein (g) | 26.0 | 33.4 | 31.1 | 26.0-34.1 |
| Fat (g) | 36.2 | 37.8 | 42.7 | 36.2-42.7 |
| CHO* (g) | 125 | 128 | 167 | 125-167 |
| % Energy (E) | % E | % E | % E | % E |
| Protein | 11 | 13 | 11 | 11-13 |
| Fat | 35 | 34 | 33 | 33-35 |
| CHO | 54 | 51 | 54 | 51-54 |

REFERENCES

Barker D J, Clark P M. Fetal undernutrition and disease in later life. Rev Reprod 1997; 2:105-112.

Law C M, Barker D J, Osmond C, Fall C H, Simmonds S J. Early growth and abdominal fatness in adult life. J Epidemiol Community Health, 1992; 46 184-18.

Barker D J. Outcome of low birthweight. Horm Res 1994; 42:223-230.

Hoet J J, Hanson M A. Intrauterine nutrition: its importance during critical periods for cardiovascular and endocrine development. J Physiol (Lond) 1999; 514:617-627.

Ozanne S E, Hales C N. The long-term consequences of intra-uterine protein malnutrition for glucose metabolism. Proc Nutr Soc 1999; 58:615-619.

Langley-Evans S C, Sherman R C, Welham S J, Nwawu M O, Gardner D S, Jackson A A. Intrauterine programming of hypertension: the role of the renin-angiotensin system. Biochem Soc Trans 1999; 27:88-93.

Tycko B, Ashkenas J. Epigenetics and its role in disease. J. Clin Invest, 2000; 105:245-246.

Patel M. S, Vadlamudi S. P and Johanning G. L, Overview of pup in a cup model: hepatic lipogenesis in rats artificially reared on a high-carbohydrate formula J. Nutr, 1993, 123: 373-377.

Hiremagalur B. K, Vadlamudi S, Johanning G. L and Patel, M. S, Long-term effects of feeding high carbohydrate diet in pre-weaning period by gastrostomy: a new rat model for obesity. Inter J Obesity, 1993, 17:495-502.

Song F, Srinivasan M, Aalinkeel R, Patel M S. Use of cDNA Array for identification of genes induced in islets of suckling rats by a high-carbohydrate nutritional intervention. Diabetes 2001; 50:2053-2060.

Aalinkeel R, Srinivasan M, Song F and Patel M S. Programming into adulthood of islet adaptations induced by early nutrition in the rat. Am J Physiol Endocrinol Metab, 2001, 281:E640-648.

Michaelsen F K and Jorgensen M. Dietary fat content and energy density during infancy and childhood, Eur J Clin Nutr, 1995, 49: 467-483.

Lapinleimu. H, Viikari J, Jokinen E, Salo P, Routi T, Leino A, Ronnemaa T, Seppanen R, Valimaki I, Simell O, Prospective randomised trial in 1062 infants of diet low in saturated fat and cholesterol. Lancet. 1995; 345:471-476

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A kit of semi solid, weaning baby food products for administration to a child during a complementary feeding period in which the child is also consuming breast milk and/or an infant formula in addition to the semi solid, weaning baby food products, the kit comprising:
at least two semi solid, weaning baby food products, wherein the combination of the at least two semi solid, weaning baby food products comprises a macronutrient content that is specific for a child in an age range of from 6 months to 8 months, and wherein the macronutrient content of the combination of semi solid, weaning baby food products and breast milk and/or infant formula comprises from about 40% to about 50% energy from fat and from about 40% to about 49% energy from carbohydrates.

2. The kit of claim 1, wherein the kit is designed for consumption of the plurality of semi solid, weaning baby food products in a single day.

3. The kit of claim 1, wherein the plurality of semi solid, weaning baby food products comprises at least one meal and at least one snack.

4. The kit of claim 1, wherein the kit contains at least one fruit-based semi solid, weaning baby food product, at least one vegetable-based semi solid, weaning baby food product, and/or at least one semi solid, weaning baby food product containing meat.

5. The kit of claim 1, wherein the kit contains at least one baby cereal.

6. A kit of semi solid, weaning baby food products for administration to a child during a complementary feeding period in which the child is also consuming breast milk and/or an infant formula in addition to the semi solid, weaning baby food products, the kit comprising:
at least two semi solid, weaning baby food products, wherein the combination of the at least two semi solid, weaning baby food products comprises a macronutrient content that is specific for a child in an age range of from 8 months to 12 months, and wherein the macronutrient content of the combination of semi solid, weaning baby food products and breast milk and/or infant formula comprises from about 38% to about 49% energy from fat and from about 41% to about 51% energy from carbohydrates.

7. The kit of claim 6, wherein the kit is designed for consumption of the plurality of semi solid, weaning baby food products in a single day.

8. The kit of claim 6, wherein the plurality of semi solid, weaning baby food products comprises at least one meal and at least one snack.

9. The kit of claim 6, wherein the kit contains at least one fruit-based semi solid, weaning baby food product, at least one vegetable-based semi solid, weaning baby food product, and/or at least one semi solid, weaning baby food product containing meat.

10. The kit of claim 6, wherein the kit contains at least one baby cereal.

11. A kit of semi solid, weaning baby food products for administration to a child during a complementary feeding period in which the child is also consuming breast milk, an infant formula, and/or growing up milk in addition to the semi solid, weaning baby food products, the kit comprising:
at least two semi solid, weaning baby food products, wherein the combination of the at least two baby food products comprises a macronutrient content that is specific for a child in an age range of from 12 months to 36 months, and wherein the macronutrient content of the combination of semi solid, weaning baby food products and breast milk, infant formula, and/or growing up milk comprises from about 30% to about 47% energy from fat and from about 42% to about 55% energy from carbohydrates.

12. The kit of claim 11, wherein the plurality of semi solid, weaning baby food products comprising at least three meals and at least two snacks.

13. The kit of claim 11, wherein the combination of baby food products present in the kit comprises a macronutrient content that is specific for a child in an age range of from 12 months to 18 months, and wherein the macronutrient content of the combination of baby food products in the kit comprises from about 36% to about 47% energy from fat and from about 42% to about 51% energy from carbohydrates.

14. The kit of claim 11, wherein the combination of baby food products present in the kit comprises a macronutrient content that is specific for a child in an age range of from 18 months to 24 months, and wherein the macronutrient content of the combination of baby food products in the kit comprises from about 34% to about 44% energy from fat and from about 44% to about 53% energy from carbohydrates.

15. The kit of claim 11, wherein the combination of baby food products present in the kit comprises a macronutrient content that is specific for a child in an age range of from 24 months to 36 months, and wherein the macronutrient content of the combination of baby food products in the kit comprises from about 30% to about 41% energy from fat and from about 46% to about 55% energy from carbohydrates.

16. The kit of claim 11, wherein the combination of baby food products present in the kit comprises a macronutrient content that is specific for a child aged about 36 months, and wherein the macronutrient content of the combination of baby food products in the kit comprises from from about 30% to about 35% energy from fat and from about 50% to about 55% energy from carbohydrates.

17. The kit of claim 11, wherein the kit contains at least one fruit-based semi solid, weaning baby food product, at least one vegetable-based semi solid, weaning baby food product, and/or at least one semi solid, weaning baby food product containing meat.

18. The kit of claim 11, wherein the kit contains at least one baby cereal.

19. A kit of semi solid, weaning baby food products for administration to a child during a complementary feeding period in which the child is also consuming breast milk, an infant formula, and/or growing up milk in addition to the semi solid, weaning baby food products, the kit comprising:
　　at least two semi solid, weaning baby food products suitable for an infant in a developmental stage comprising from about 6 months to about 36 months of age, the at least three semi solid, weaning baby food products combined for consumption within a single day so as to provide an optimal daily energy intake, wherein a macronutrient content of the combination of the at least two baby food products and breast milk, infant formula, and/or growing up milk comprises:
　　(a) a fat content that is a percentage of the energy intake in a range having a lower end calculated by the Formula:

$y=-1/3x+42$ and an upper end calculated by the Formula:

$y=-1/2x+53$ wherein y is the percent energy intake from fat and x is the age of the child in months; and
　　(b) a carbohydrate content that is a percentage of the energy intake in a range having a lower end calculated by the Formula:

$y=1/3x+38$ and an upper end calculated by the Formula:

$y=1/5x+47.8$ wherein y is the percent energy intake from carbohydrate and x is the age of the child in months.

20. The kit of claim 19, wherein the at least two semi solid, weaning baby food products comprises at least one meal and at least one snack.

21. The kit of claim 19, wherein the kit contains at least one fruit-based semi solid, weaning baby food product, at least one vegetable-based semi solid, weaning baby food product, and/or at least one semi solid, weaning baby food product containing meat.

22. The kit of claim 19, wherein the kit contains at least one baby cereal.

* * * * *